(12) United States Patent
Jones

(10) Patent No.: US 6,873,680 B2
(45) Date of Patent: Mar. 29, 2005

(54) METHOD AND APPARATUS FOR DETECTING DEFECTS USING DIGITAL RADIOGRAPHY

(75) Inventor: James Wayne Jones, The Woodlands, TX (US)

(73) Assignee: Siemens Westinghouse Power Corporation, Orlando, FL (US)

(*) Notice: Subject to any disclaimer, the term of this patent is extended or adjusted under 35 U.S.C. 154(b) by 154 days.

(21) Appl. No.: 10/428,695

(22) Filed: May 2, 2003

(65) Prior Publication Data

US 2004/0218715 A1 Nov. 4, 2004

(51) Int. Cl.[7] .............................................. G01B 15/06
(52) U.S. Cl. ...................... 378/58; 378/57; 250/341.8; 250/358.1; 382/141; 382/149; 382/152
(58) Field of Search .................... 378/5, 16, 21–27, 378/57, 58, 62, 63, 87, 98.9, 98.11, 98.12, 207; 250/341.8, 358.1; 382/100, 132, 141, 149, 152

(56) References Cited

U.S. PATENT DOCUMENTS

| | | | |
|---|---|---|---|
| 4,351,185 A | | 9/1982 | Garcia |
| 4,365,339 A | | 12/1982 | Pavkovich et al. |
| 4,600,998 A | | 7/1986 | Huet |
| 5,032,990 A | | 7/1991 | Eberhard et al. |
| 5,119,408 A | * | 6/1992 | Little et al. .................. 378/4 |
| 5,164,971 A | | 11/1992 | Peyret et al. |
| 5,253,282 A | * | 10/1993 | Pelc .......................... 378/98.2 |
| 5,400,381 A | | 3/1995 | Steude et al. |
| 5,805,721 A | | 9/1998 | Vuylsteke et al. |
| 5,844,243 A | | 12/1998 | Lee et al. |
| 6,025,599 A | | 2/2000 | Lee et al. |
| RE37,536 E | | 2/2002 | Barnes |
| 6,459,760 B1 | * | 10/2002 | D'Ambrosio ................ 378/43 |
| 6,495,833 B1 | * | 12/2002 | Alfano et al. ............ 250/341.8 |
| 6,597,759 B2 | * | 7/2003 | Mazess et al. ................ 378/53 |

OTHER PUBLICATIONS

"Amorphous Selenium Direct Radiography for Industrial Imaging"; Proceedings of Computerized Tomography for Industrial Applications and Image Processing in Radiology; Mar. 15–17, 1999, Berlin, Germany; DGZfP–Proceedings BB 67–CD; pp. 1–10.

Davis, Anthony W., et al; "An Analysis of Industrial Non-destructive Testing Employing Digital Radiography as an Alternative to Film Radiography"; ESA–MT Nondestructive Testing and Evaluation Team, Los Alamos National Laboratory; Mar. 1, 2000; pp. 1–17.

AGFA RADView Non–Destructive Testing; downloaded from http://ndt.agfa.com/bu/ndt/index.nsf/EN/directradiography.htm, Jan. 2, 2003.

* cited by examiner

*Primary Examiner*—Allen C. Ho

(57) ABSTRACT

A digital radiography apparatus (10) and process for providing images of an object, for example, an exhaust transition duct (12) comprising a core material and an overlying thermal barrier layer, to detect surface and interior defects within the duct (12). Incident energy is provided by an energy source (30), transmitted through the object (12), and sensed by a sensor (32). An image of the object (12) is formed by processing the signal from the sensor (32) in a signal processor (34) and displaying the image on a display (36) for determining defects in the object (12).

21 Claims, 1 Drawing Sheet

METHOD AND APPARATUS FOR DETECTING DEFECTS USING DIGITAL RADIOGRAPHY

FIELD OF THE INVENTION

The present invention relates generally to digital radiography, and more particularly to the use of digital radiography to detect defects in metal parts.

BACKGROUND OF THE INVENTION

Rapid, efficient and accurate inspection of large industrial and machine parts is critical to determining defect existence and severity. Based on the inspection results, the user can determine whether the part can be effectively repaired or requires replacement. One such part of interest is the exhaust transition duct that carries hot exhaust gases from the combustion zone of a combustion turbine to external exhaust processing components. The gas combustion process imparts rotational energy to a shaft of an electrical generator, producing electricity for a power delivery system or for an industrial site. Certain gas turbines include as many as 16 exhaust transition ducts, each duct including as many as 20 individual and differently shaped panels welded together to form the duct. The panel material typically comprises a nickel-based super alloy.

During gas turbine operation, hot hydrocarbon-laden exhaust gasses, with temperatures up to 2000° F., pass through the exhaust duct. These severe environmental conditions can cause the ducts to develop various defect types and sizes, both in the panel surfaces and in the welds between the individual panels. The gases are corrosive and experience wide temperature excursions, causing the ducts to flex, erode and crack. A thermal barrier layer overlies the duct exterior surface to retain heat within the duct structure and avoid heating (and thus damaging) proximate components of the gas turbine and electrical generator, such as wires and electrical devices. Conventionally, the thermal barrier comprises two materials, a metallic substrate or bond coat, and a ceramic topcoat. The thermal barrier is applied using a thermal spray process with stringent process controls. Thus application of the thermal barrier layer can be a time-consuming and relatively expensive process.

To ensure the ducts retain the required structural integrity, they are subjected to frequent inspections designed to identify defects. The defects are classified according to defect size, the number of defects within a predetermined distance of each other, and the location of a defect relative to a particular feature of the duct (e.g., features such as the inlet face or the exhaust mouth). Once the defects have been identified and classified, predetermined threshold defect parameters are consulted to determine whether the defects impair the duct structural integrity, and whether the duct should be repaired or replaced.

Prior art surface inspection processes useful for detecting defects in metal objects, such as the exhaust transition ducts, include visual inspection and dye penetrant inspection. When employed to inspect the exhaust gas transition ducts, both of these inspection techniques require removal of the thermal barrier layer prior to performing the inspection. If the detected defects are of such a character that they can be repaired, then following the repair the thermal barrier coating must be reapplied.

The nature of a visual inspection process is self-evident. After the thermal barrier layer is removed, a repair technician visually inspects the individual duct panels and the joining welds to identify cracks, discontinuities or other defects. If not identified and not timely repaired, such cracks or defects can grow; eventually causing a breach in the panel through which the hot exhaust gases can escape. Only surface defects are detectable according to this technique. The visual inspection process is subjective and dependent on the skill of the inspector.

The known non-destructive dye penetrant inspection technique requires a clean material surface, free of surface films and oxides. Thus the barrier layer of the exhaust transition duct must be removed. The area is then flooded with a penetrant composition (commonly comprising a light hydrocarbon oil or an emulsifiable oil) that contains either a visible penetrant (typically a red dye) or a fluorescent dye. The penetrant is permitted to stand on the surface of the material for a sufficient time to seep into surface discontinuities or cracks that extend to the surface. The excess penetrant is removed, and after drying, a developer is applied to the surface. The developer may take the form of finely ground solid particles or a dispersion of solid particles in a liquid or an aerosol. The deposition of these particles immobilizes the penetrant and renders it contrastingly visible. Inspection of the piece is then conducted under ordinary white light, in the case of a visible penetrant, or under ultraviolet radiation, in the case of a fluorescent dye penetrant. Like the visual inspection process, only the surface defects are detectable, and the efficacy of the process depends on the inspector's skill level.

It is noted that both the visual and dye penetrant inspection processes reveal only surface defects. Neither the inwardly facing surfaces nor the interior regions of the transition duct panels is inspectable using these processes. In an effort to overcome certain of these limitations, the duct can be subjected to a heat-treating process prior to the visual or dye penetrant inspection. Heating the duct may cause internal defects to migrate to the surface, where they can be identified according the visual or dye penetrant tests.

X-ray radiography is another known non-destructive inspection process for producing an image representing the density of an object, such as a panel of the exhaust transition ducts discussed above. Low-density regions, such as voids, are visible in the radiograph due to their contrast with high-density regions. High energy radiation, typically x-rays or gamma-rays, is transmitted through the object, attenuated as a function of the object density along the energy path between the source and the detector, and converted into light of a corresponding intensity as the transmitted rays impinge on a detector screen. The screen is conventionally constructed with phosphor particles that absorb the transmitted x-rays and convert them into visible light or ultraviolet radiation. A photographic film, conventionally comprising a silver halide emulsion layer, is responsive to the visible light or the ultraviolet radiation for changing the characteristics of the emulsion layer. The film is developed to reveal an image conforming to the transmission (or conversely, attenuation) of the incident energy passing through the object. Use of a film system is preferred as film exhibits a higher sensitivity to the secondary light or ultraviolet radiation emitted by the detector screen than to the direct impact of the transmitted x-rays.

There are known limitations to the film x-ray radiography technique. The resulting image is static and based solely on the source x-ray characteristics. If it is desired to create a different image to discern different details of the object, the image must be re-shot using source x-rays of a different energy level and/or incident from a different direction. Because more dense regions of the object induce greater attenuation of the x-ray beam, object density can be determined from the resulting film product. However, an x-ray does not indicate density as a function of depth through the object, that is, along the incident x-ray beam. The x-ray film thus provides only a two-dimensional representation of a three-dimensional object. If an x-ray reveals a denser region in a corner of the object, for example, it is not possible to determine whether that denser region is on the incident surface (i.e., with respect to the impinging x-ray) of the object, on the surface where the x-ray exits the object or in an interior region between these two surfaces.

Additionally, since the various duct surfaces and the thermal barrier layer present several different thicknesses to an impinging x-ray, it is necessary to use x-rays of different source energies dependent upon the thickness of the imaged region. The welds, for example, present a thicker material than the panels and thus require a higher energy incident x-ray to produce a usable image. However, it is known that higher energy x-rays reduce the contrast between regions of unequal density, thus reducing the ability to distinguish regions of different densities.

Further, to image a complex three-dimensional structure such as the transition exhaust duct, it is necessary to reposition both the receiving film and the x-ray source prior to each image. All of these complexities associated with x-ray radiography contribute to longer inspection times and therefore increased inspection costs.

BRIEF SUMMARY OF THE INVENTION

The present invention comprises a method for detecting internal and external defect features of an object, wherein the object comprises a metallic core material and a thermal barrier surface layer that prevents visual inspection of the core material. The object is subjected to incident energy, and the energy transmitted through the object is sensed and converted to representative digital data. The data is processed to form an image of the object. The position of the object relative to the incident energy is adjusted so that an image of predetermined regions of the object can be captured. The image parameters are controlled to remove the effects of the thermal barrier coating to allow detection of the defects.

BRIEF DESCRIPTION OF THE DRAWINGS

The foregoing and other features of the invention will be apparent from the following more particular description of the invention, as illustrated in the accompanying drawings, in which like reference characters refer to the same parts throughout the different figures. The drawings are not necessarily to scale, emphasis instead being placed upon illustrating the principles of the invention.

DETAILED DESCRIPTION OF THE INVENTION

Figure 1:
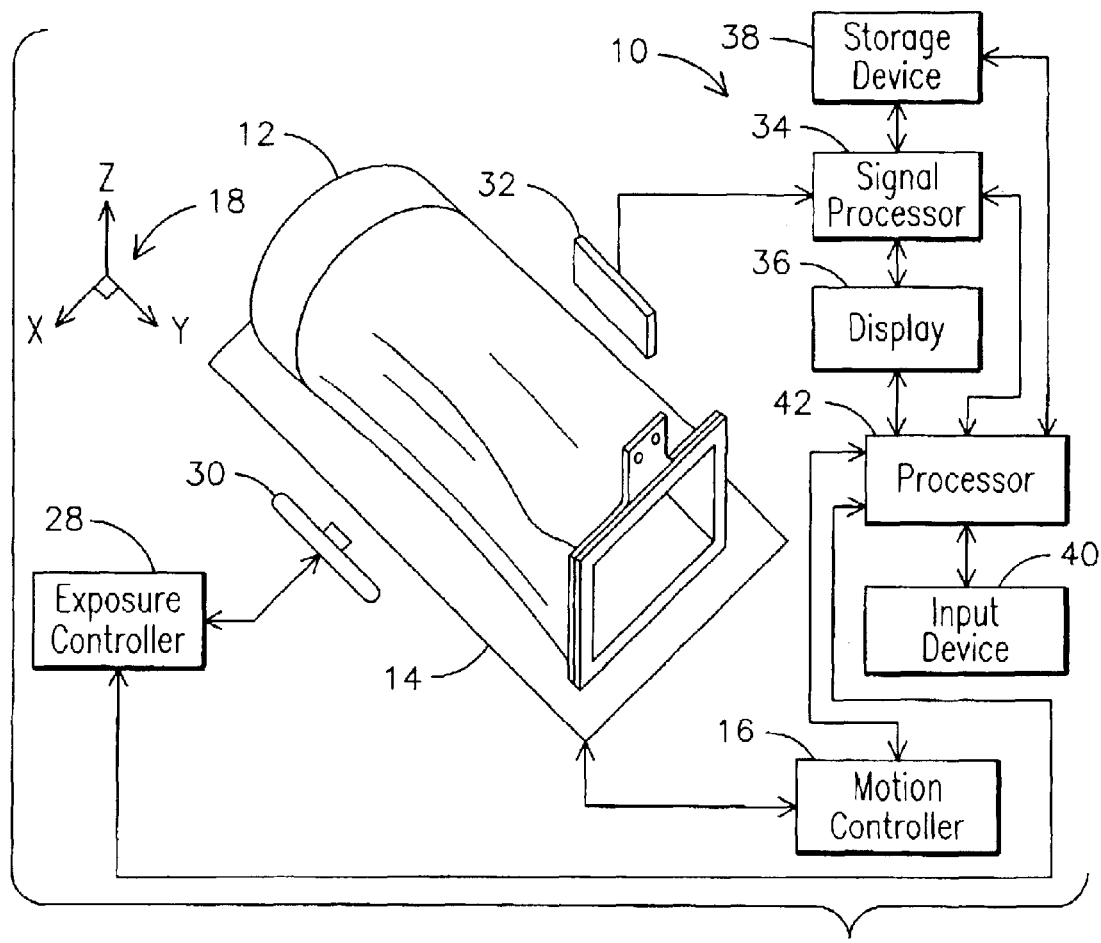
FIG. 1 is a pictorial representation of an exhaust transition duct and the digital radiography components for conducting an inspection according to the teachings of the present invention.

Before describing in detail the particular digital radiography based inspection method in accordance with the present invention, it should be observed that the present invention resides primarily in a novel and non-obvious combination of hardware elements and method steps. Accordingly, these elements and steps have been represented by conventional elements and steps in the drawings, showing only those specific details that are pertinent to the present invention so as not to obscure the disclosure with details that will be readily apparent to those skilled in the art and having the benefit of the description herein.

The use of digital radiography techniques for inspecting material pieces, such as the gas turbine transition exhaust ducts, offers several advantages over prior art techniques. The variability and subjectivity of the inspection results encountered with the visual and dye penetrant inspection tests described above are obviated by the creation of a stored permanent visual record that allows multiple interpretations of a single image. Thus, more consistent interpretative results are produced from the inspection process. Dye penetrant and visual inspection tests are subject to variability in the inspection results due to numerous factors affecting interpretation of the liquid penetrant results and the subjective visual determinations derived therefrom.

Use of an automated digital radiography system comprising a source and capture media movable relative to the piece under inspection precludes the labor-intensive process of physically repositioning the component for each exposure. In this regard, there is a particularly notable improvement as compared with x-ray radiography, where the number of required exposures and the number of required component moves are significantly greater. Also, digital radiography allows earlier identification of internal aberrations that can later grow into problematic defects, compared with the prior art processes that provide detection of surface defects only. The early and accurate detection of internal defects offers more rapid and accurate repair, leading to extended component service life. More information is also produced from a digital radiograph than an x-ray radiograph, due to the broader dynamic range of output signal levels provided by the capture medium. The digital capture of the image allows image enhancement through software image manipulation, and image data transfer to remote locations for analysis and storage. As applied to the inspection of exhaust transition ducts as described herein, the use of digital radiography obviates the need to remove the thermal barrier layer prior to inspection, saving the time and expense associated with removing the thermal barrier and reapplying the barrier after the repairing the transition duct.

Generally, in digital radiography, an x-ray source emits a beam of x-rays that are incident on a target. The x-ray radiation passing through the target is intensity modulated due to the differential absorption of x-rays by various regions and constituent parts and elements of the target, that is, due to differential densities within the object. The x-rays transmitted through the target are captured and stored on an imaging or capture element, comprising a plurality of pixels. The magnitude of the electrical charge at each image pixel is read from the imaging element, converted to a digital value and stored for processing and analysis in a computer. The data is processed to form representative image for display and may also undergo image processing, such as filtering and contrast enhancement, to facilitate interpretation of the image, and especially to discern details of target regions below the target surface.

FIG. 1 illustrates the elements of a digital radiography inspection tool 10, for inspecting a component, such as an exhaust duct 12, positioned on a holding fixture represented generally by an illustrated holding fixture 14. Conventionally, the exhaust duct 12 comprises a plurality of differently shaped welded panels. The panel material typically comprises a nickel-based super alloy with an overlying thermal barrier layer. The exhaust duct 12 remains stationary relative to the holding fixture 14 while the position of the holding fixture 14 is controlled by a motion controller 16. Accurate and controllable positioning is important for accurate radiographic results. When the inspection begins, the holding fixture 14 is moved to a pre-determined home position under control of the motion controller 16. The home position serves as a reference position for all subsequent orientations of the exhaust duct 12 during the inspection process. In one embodiment, twenty-two overlapping radiographic images are created to provide a complete inspection of the exhaust duct 12. For each of the plurality of exposures, the holding fixture 14 is moved to a specific set of predetermined coordinates, with reference to the x-y-z coordinate system 18 as illustrated.

At each predetermined coordinate position, an exposure program is executed by an exposure controller 28 for controlling the radiation emitted by a source 30 to expose a region of the exhaust duct 12 and acquire an image of that region. The controlled radiation parameters include one or more of the exposure duration, exposure energy and the x-ray frequency. The distance between the source 30 and the exhaust duct 12 can also be varied to obtain the required image. Different radiation parameters can be established for each region to be imaged, dependent on the physical characteristics of the region. Also, multiple exposures can be made of a single region, using different radiation parameters for each exposure.

The radiation transmitted through the exhaust duct 12 is detected by a detector 32 for producing an output signal representing the intensity of the transmitted energy, as attenuated by the imaged regions of the exhaust duct 12. Conventionally, for capturing the x-ray pattern the detector 34 comprises an x-ray sensitive phosphor, intensifier, or photoconductive material that converts the x-rays into electrical signals for processing and display as described below. Other detector types convert the received x-rays to visible light for capturing and digitizing.

The output signal from the detector 32 representing the received radiation is input to a signal processor 34 for digitizing, analysis, display on a display 36, and/or storage in a storage device 38. Operation of the signal processor 34 is discussed herein below. After an image has been captured, the motion controller 16 repositions the holding fixture 14 for moving the exhaust duct 12 to the next exposure position, after which another exposure is acquired. Overall control of the inspection tool 10 is executed by a processor 42 according to user-supplied instructions.

The signal processor 34 operates on the output signal from the detector 32 to create a viewable image and enhance certain image features to improve the display of subtle image variations. These image enhancements permit more accurate interpretation of the results by an inspector viewing an image on the display 36. For example, the digitized image representation can be processed to identify different defect types at different depths within a panel of the exhaust duct 12. The signal processor 34 operates on the image data to provide such image manipulations and enhancements not previously available using conventional x-ray radiographic imaging techniques, permitting the inspector to "see through" different material layers, thicknesses and types. Such image signal processing techniques are know to those skilled in the art, and include frequency and spatial filtering, brightness and sharpness control, resolution adjustments, and contrast enhancement or stretching (wherein the full dynamic range of the output medium, such as the display 36, is utilized to reveal the intensity variations of the x-ray transmitted through the exhaust duct 12). During the display interpretation process the inspector can adjust the image parameters to display varying degrees of contrast enhancement, filtering, etc., via an input device 40.

Once the defects have been detected, they are classified according to defect size, the number of defects within a predetermined distance of each other, and the location of a defect relative to a particular feature of the duct (e.g., features such as the inlet face or the exhaust mouth). Predetermined threshold defect parameters are consulted to determine whether the defects impair the duct structural integrity, and further to determine whether the duct should be repaired or replaced. The defect identification process and consultation of the threshold defect parameters, can be executed automatically by the processor 42 of the inspection tool 10, or manually by an inspector while viewing a captured inspection image.

The digital radiography inspection tool 10 also provides computed tomography capabilities for producing two-dimensional cross sectional images of the three-dimensional exhaust duct 12. The tomographic capability provides an image of the internal features of the exhaust duct 12, allowing internal structural analysis by the inspector. As is known to those skilled in the art, a tomographic system includes a source and a sensor disposed on the opposite side of the exhaust duct 12 from the source. If the source 30 and the detector 32 are controlled to translate axially along and rotate around the exhaust duct 12, a plurality of image "slices" is acquired. Processing of these image slices in the signal processor 42 produces a plurality of parallel two-dimensional representations of the image slice planes. Thus the inspector can analyze the internal features of the exhaust duct 12 through the plurality of exhaust duct 12 plains. The signal processing image enhancement techniques described above can also be applied to the image slices. The signal processor 34 can also display images of the exhaust duct 12 based on two or more acquired images of the same region. These acquired images can be added, subtracted, or related according to more complex mathematical functions to produce an image display providing the inspector with additional information from which to determine the existence of defects.

The incident energy can be selected from among light, heat, sound, transmissive ultrasound, electromagnetic radiation, x-rays, gamma rays, and sub-atomic particles including electrons, protons, neutrons and heavy ions. As is known by those skilled in the art, for the digital radiography inspection process of the present invention, the form of energy can be advantageously selected to reveal specific defect types and sizes.

Thus, the ability to accurately control exposure parameters at the various duct orientations provides consistent inspection results and eliminates the subjective variability associated with the prior art liquid penetrant and visual inspection methods. Due to the more accurate defect size and location information provided according to the present invention, including internal defect information that has not been available using prior art techniques, the defect repair processes can be more accurately designed and executed.

Figure 2:
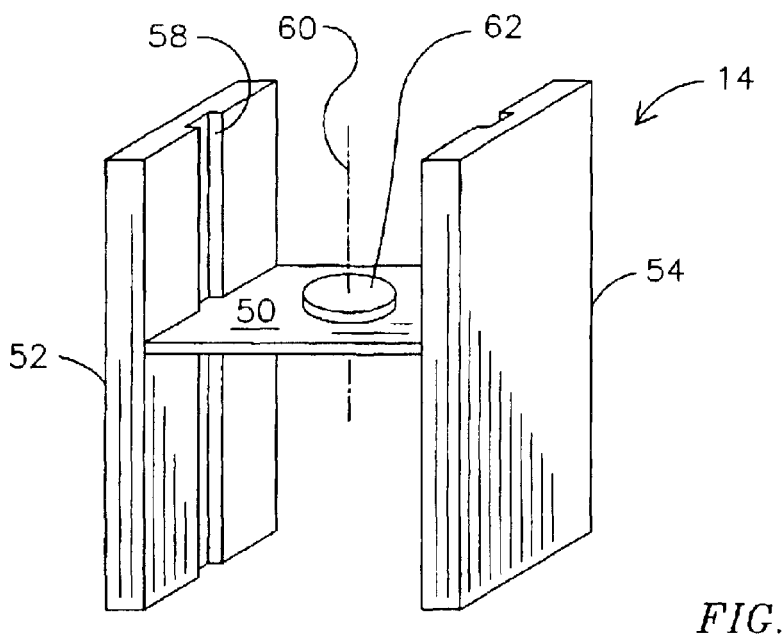
FIG. 2 is a perspective pictorial representation of a holding fixture suitable for carrying the exhaust transition duct of FIG. 1 during the inspection process.

A holding fixture 14, suitable for use during the digital radiography inspection process according to the present invention, is illustrated generally in FIG. 2. A table 50 is movably supported between two vertical supports 52 and 54. The motion controller 16 provides control signals to motion-inducing devices, such as electric motors (not shown) within the holding fixture 14, for imparting motion to the exhaust duct 12 positioned on a turntable 62. In particular, the table 50 translates vertically along a track 58 in each vertical support 52 and 54, and can be angularly adjusted relative to a vertical axis 60. A turntable 62 imparts rotational motion to the exhaust duct 12 relative to the axis 60.

Use of the digital radiography apparatus and method according to the present invention obviates the aforementioned requirement of removing the thermal barrier layer prior to conducting the prior art inspection processes. Absent the object preparation steps, the inspection can be conducted faster and more efficiently. Additionally, the present invention provides an improved display of the duct 12, with user adjustable exposure parameters for more accurate and efficient detection of defects.

Although the teachings of the invention have been described with reference to the exhaust duct 12, it is recognized that the teachings can be applied to other components, resulting in the attendant inspection and repair advantages as described above.

While the invention has been described with reference to preferred embodiments, it will be understood by those skilled in the art that various changes may be made and equivalent elements may be substituted for elements thereof without departing from the scope of the present invention. The scope of the present invention further includes any combinations of the elements from the various embodiments set forth herein. In addition, modifications may be made to adapt the teachings of the present invention to a particular situation without departing from its scope. Therefore, it is intended that the invention not be limited to the particular embodiment disclosed as the best mode contemplated for carrying out this invention, but that the invention will include all embodiments falling within the scope of the appended claims.

What is claimed is:

1. A method for detecting internal features of an object, wherein the object comprises a metallic core material and a thermal barrier layer that prevents visual inspection of the core material, the method comprising:
   subjecting the object to incident energy;
   sensing the energy transmitted through the object;
   converting the sensed energy into representative digital data;
   processing the digital data to form an image of the object, wherein the image is characterized by image parameters;
   positioning the object relative to the incident energy to image regions of the object; and
   controlling the image parameters to remove the effects of the thermal barrier layer.

2. The method of claim 1 wherein the incident energy is selected from among light, heat, sound, transmissive ultrasound, electromagnetic radiation, x-rays, gamma rays, and sub-atomic particles further comprising electrons, protons, neutrons and heavy ions.

3. The method of claim 1 wherein the incident energy is defined by a plurality of exposure parameters, further comprising adjusting one or more of the plurality of exposure parameters.

4. The method of claim 3 wherein the plurality of exposure parameters comprise exposure duration, incident energy frequency, and incident energy intensity.

5. The method of claim 3 further comprising acquiring multiple images of a region of the object, wherein the step of adjusting is executed between acquiring successive multiple images of the region.

6. The method of claim 3 wherein each of the regions is associated with a predetermined set of exposure parameters.

7. The method of claim 1 wherein the step of controlling the image parameters further comprises removing the effects of the thermal barrier coating to analyze features of an interior of the core material.

8. The method of claim 1 wherein the step of controlling the image parameters further comprises removing the effects of the thermal barrier coating to analyze features on a surface of the core material.

9. The method of claim 1 wherein the step of controlling the image parameters further comprises enhancing the visibility of internal features.

10. The method of claim 1 further comprising analyzing the digital data to detect an anomaly in the core material.

11. The method of claim 10 wherein the anomaly is declared to indicate a defect if the size of the anomaly is greater than a predetermined value.

12. The method of claim 10 wherein the anomaly is declared to indicate a defect if the number of anomalies within a defined region of the object is greater than a predetermined number.

13. The method of claim 10 wherein the anomaly is declared to indicate a defect if the anomaly is within a predetermined distance of a defined region of the object.

14. The method of claim 1 wherein the object has a non-uniform thickness.

15. The method of claim 1 wherein the parameters of the incident energy are varied to permit analysis of an interior of the core material.

16. The method of claim 1 further comprising displaying the image.

17. The method of claim 1 further comprising repeating the step of positioning the object such that the digital data represents substantially the entire object.

18. An apparatus for detecting internal features of an object, wherein the object comprises a metallic core and a thermal barrier that prevents visual inspection of the core, the apparatus comprising:
   an energy source for transmitting incident energy toward the object;
   a sensor for sensing the energy transmitted through the object;
   a signal processor for converting the sensed energy into representative digital data and for processing the digital data to form an image of the object, wherein the image is characterized by image parameters;
   a holding fixture for positioning the object relative to the incident energy; and
   wherein the signal processor controls the image parameters to remove the effects of the thermal barrier.

19. The apparatus of claim 18 further comprising a storage device for storing the digital data.

20. The apparatus of claim 18 further comprising a user-operated input device, wherein the signal processor is responsive to the input device for controlling the image parameters.

21. The apparatus of claim 18 further comprising a motion controller, wherein the holding fixture is responsive to the motion controller for positioning the object relative to the incident energy to image regions of the object.

* * * * *